United States Patent [19]
Kim et al.

[11] Patent Number: 5,516,927
[45] Date of Patent: May 14, 1996

[54] 2-NITROBENZOYL-3-SILYLOXYAMINOACRYLATE DERIVATIVES AND METHOD FOR THE PREPARATION OF THE SAME

[75] Inventors: Yousoung Kim; Soon Bang Kang; Seonhec Park, all of Seoul, Rep. of Korea

[73] Assignee: Korea Institute of Science and Technology, Seoul, Rep. of Korea

[21] Appl. No.: 453,007

[22] Filed: May 26, 1995

[30] Foreign Application Priority Data

May 28, 1994 [KR] Rep. of Korea ............... 94-11747

[51] Int. Cl.⁶ .................................................. C07F 7/10
[52] U.S. Cl. .................................................. 556/418
[58] Field of Search ............................................ 556/418

[56] References Cited

U.S. PATENT DOCUMENTS

| | | | |
|---|---|---|---|
| 4,284,776 | 8/1981 | Gruber et al. | 556/418 X |
| 4,697,026 | 9/1987 | Lee et al. | 556/418 |
| 4,728,746 | 3/1988 | Shibasaki et al. | 55/418 X |
| 5,389,619 | 2/1995 | Doetzer et al. | 556/418 X |

FOREIGN PATENT DOCUMENTS

| | | |
|---|---|---|
| 84-2141 | 8/1981 | Rep. of Korea. |
| 93-4309 | 8/1991 | Rep. of Korea. |
| 93-4310 | 8/1991 | Rep. of Korea. |
| 93-10027 | 11/1991 | Rep. of Korea. |
| 93-10041 | 11/1991 | Rep. of Korea. |
| 93-12787 | 12/1991 | Rep. of Korea. |

OTHER PUBLICATIONS

Egawa, Hiroshi, et al. (1986) "A New synthesis of 7H–Pyridol [1,2,3–de] [1,4] benzoaxazine Derivatives Including an Antibacterial Agent, Ofloxacin", *Chem. Pharm. Bull* 34(10):4098–4102.

*Primary Examiner*—Paul F. Shaver
*Attorney, Agent, or Firm*—Townsend and Townsend and Crew

[57] ABSTRACT

There are disclosed 2-benzoyl-3-aminoacrylate derivatives of formula I and methods for the preparation of the same. The compounds can be used as starting materials to synthesize benzoxazine derivatives, potent antibacterial compounds.

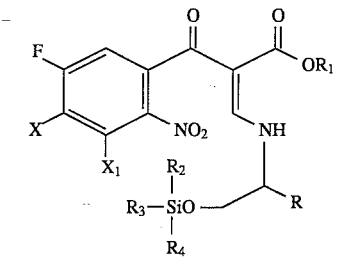

8 Claims, No Drawings

2-NITROBENZOYL-3-SILYLOXYAMINOACRYLATE DERIVATIVES AND METHOD FOR THE PREPARATION OF THE SAME

BACKGROUND OF THE INVENTION

In Japanese Patent Nos. 87215591 and 8798685, and European Patent No. 225552, there are described a number of methods for preparing pyrido benzoxazine derivatives having antibacterial activity. Further, similar antibacterially active compounds to those supra patent and their preparation methods are disclosed in Korean Patent Publication No. 84-2141 and Korean Patent Laid-Open Publication Nos. 92-22050, 93-4309, 93-4310, 93-10027, 93-10041 and 93-12787.

DESCRIPTION OF THE INVENTION

The present invention relates to novel compounds useful to synthesize antibacterially active benzoxazine isomers. More particularly, the present invention is concerned with 2-nitrobenzoyl-3-silyloxyaminoacrylate derivatives having the following general formula I, the stereoisomeric forms thereof, or the salt thereof:

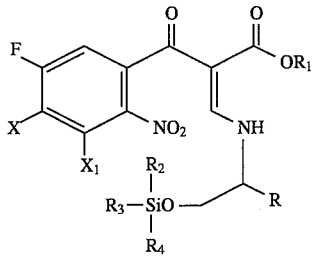

wherein
X is halogen;
$X_1$ and $X_2$ are independently selected from halogen and nitro; and
R, $R_1$ and $R_2$ each is an alkyl group containing 1 to 4 carbon atoms.

Surprisingly, this compound can be used as a starting material to synthesize pyrido benzoxazine carboxylic acid dericatives, represented by the following formula II, which are intermediates for preparation of potent antibacterial agents.

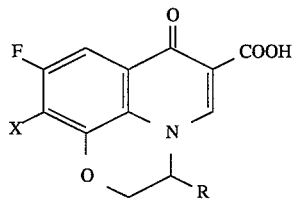

wherein X is a fluorine or chlorine atom and R is an alkyl group containing 1 to 4 carbon atoms.

The compound of formula I can proceed to the formula II in only two steps, which is suggested in Korean Patent Application No. 11749/94 to the present inventors, filed on 28 May, 1994.

Therefore, in an aspect of the present invention, there are provided novel starting materials, 2-nitrobenzoyl-3-silyloxyaminoacrylate derivatives of the general formula I, useful to synthesize the antibacterially active pyrido benzoxazine derivatives.

The present invention also is concerned with a method for preparing the compounds of formula I.

In accordance with another aspect of the present invention, there is provided a method for the preparation of the compounds of formula I.

The compounds of formula I can be obtained by reacting a novel acrylate derivative of the following general formula III:

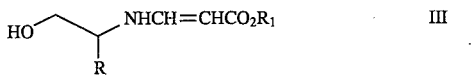

wherein R is an alkyl group containing 1 to 4 carbon atoms and $R_1$ is an alkyl or allyl group containing 1 to 8 carbon atoms, with a silyl compound of the following formula IV

in an organic solvent in the presence of a suitable base, to give a novel silylacrylate derivative of the following formula V:

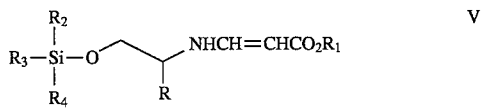

wherein R, $R_1$, $R_2$, $R_3$ and $R_4$ each is as defined above; and reacting the novel silylacrylate derivative of formula V with a 2-nitrobenzoyl chloride derivative of the following formula VI:

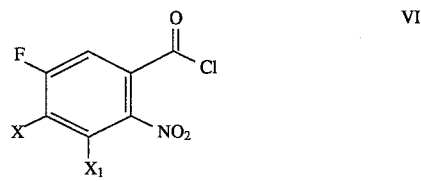

wherein X is halogen; and $X_1$ is halogen and nitro, in the presence of a suitable base.

The starting material for the 2 nitrobenzoyl 3 silyloxyaminoacrylate derivative is in detail described in Korean Patent Application No. 5974/94 to the present inventors, filed on May 24, 1994, along with preparation method of the same.

In order to help understand the present invention, the preparation method of the present invention is summarized in the following scheme.

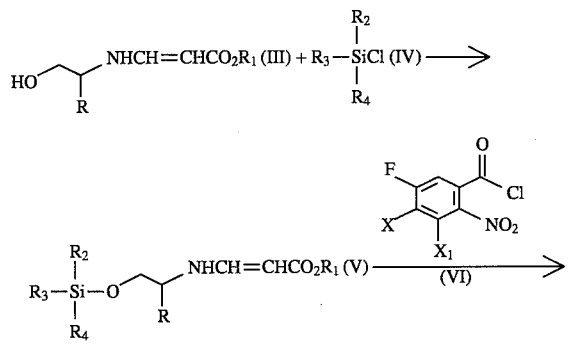

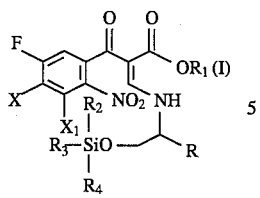

In accordance with a further aspect of the present invention, there is provided a novel compound of formula V, an intermediate useful to prepare the compound of formula I.

In accordance with a still further aspect of the present invention, there is provided a method for preparing a novel compound of formula V.

As the organic solvent effective for the reaction of the compound of formula III with the compound of formula IV, there is used dimethylformamide, tetrahydrofuran, methylenechloride, acetonitrile, benzene or toluene. In this organic solvent, the compound of formula III is stirred along with the compound of formula IV at a reaction temperature of 0° to 30° C. for 1 to 24 hours, in the presence of base, such as pyridine, triethylamine, 2,6-lutidine, 4-dimethylaminopyridine, imidazole, 1,8-diazabicyclo[5.4.0]undec-7-ene, and 1,5-diazabicyclo[4.3.0]non-5ene. When carrying this reaction, the equivalent ratio of the compound of formula II to the compound of formula III to the base is preferably in a range of 1:1.1:1.2 to 1:1.2:1.5.

With regard to reaction of the silylacrylate derivative of formula V with the 2-nitrobenzoyl chloride derivative of formula VI, it is carried out in a organic solvent, such as methylene chloride, acetonitrile, diethylether, ethylene chloride, dimethylformamide, tetrahydrofuran, and chloroform. Preferred base for this reaction includes triethylamine, pyridine, 4-dimethylaminopyridine, imidazole, 2,6-lutidine, 1,8-diazabicyclo[5.4.0]undec-7-en and 1,5-diazabicyclo[4.3.0]non-5-en. In the organic solvent, the compound of formula V is reacted with the compound of formula VI at a temperature of 0° to 100° C. for 0.5 to 3 hours in the presence of the above-mentioned base, so as to give 2-nitrobenzoyl-3-silyloxyaminoacrylate derivative of formula I. In this reaction, the equivalent ratio of the compound of formula V to the compound of formula VI to the base is preferably in a range of 1:1.05:1.1 to 1:1.1:1.2.

The products of those reactions including 2-nitrobenzoyl-3-silyloxyaminoacrylate derivatives of formula I and silylacrylate derivative of formula V can be separated and purified by conventional techniques, such as evaporation, filtration, extraction, chromatography, distillation and the combinations thereof. For example, the mixture of reactants is initially dried under reduced pressure to condense it. The resultant residual matter is added in a mixture of an organic solvent, such as dimethyl chloride, chloroform, diethylether or ethylacetate, and water and then stirred. Thereafter, the organic solvent is condensed to leave a product. In case of the mixture of product and by-products, further purification may be performed by chromatography, re-distillation or recrystallization.

The preferred embodiments of the present invention will now be further described with reference to specific examples. Unless otherwise stated all percentage, part and ratio therein are by weight.

EXPERIMENTAL PART

A. Preparation of Intermediate

Example 1

Ethyl 3-(1-t-butyldimethylsilyloxyprop-2-ylamino)acrylate (V: R=ethyl, $R_1$, $R_2$, $R_3$=methyl, $R_4$=t-butyl)

3.77 g (25 mmol) of t-butyldimethylsilylchloride (IV: $R_2$, $R_3$=methyl, $R_4$=t-butyl) and 4.04 ml (27 mmol) of 1,8-diazabicyclo[5.4.0]undec-7-ene were added in 45 ml of benzene and cooled to 0° C. To this, 10 ml of benzene containing 3.90 g (22.5 mmol) of ethyl 3-(1-hydroxyprop-2-ylamino)acrylate (III: R=ethyl, $R_1$=methyl) was slowly added dropwise. The reactant mixture was stirred at 0° C. for 1 hours stirred at room temperature for 15 hours. Thereafter, the resulting reaction system was washed with 10 ml of 0.1N aqueous hydrochloric acid solution, 10 ml of saturated aqueous sodium bicarbonate solution, 10 ml of water and 5 ml of saturated saline water, in due order and then, dried over magnesium sulfate.

After completion of the reaction, the solvent was removed under reduced pressure (25° C./10 mmHg), to give 6.37 q of oily object product (yield 98.5%).

Analysis of the product revealed that Z and E isomers were present in a ratio of 6:4 therein.

b.p.: 80–90° C./1.6 mmHg

IR (NaCl) $cm^{-1}$: 3327, 1670, 1616

NMR($CDCl_3$): 7.72–7.84(1H×3/5, m), 7.48(1H×2/5, dd, J=13.9H), 6.71(1H×3/5, dd, J=13.8H), 4.74(1H×2/5, d, J=13H), 4.67–4.72(1H×2/5, m), 4.44(1H×3/5, d, J=8H), 4.09(2H, q, J=7H), 3.43–3.57(2H, m), 3.27(1H, m), 1.25(3H, t, J=7H), 1.18(3H, d, J=6.6H), 0.08(9H, s), 0.034(6H, s)

Example 2

Ethyl 3-(1-t-butyldimethylsilyloxyprop-2-ylamino)acrylate (V: R=methyl, $R_1$=ethyl, $R_2$, $R_3$=methyl, $R_4$=t-butyl)

2.20 g (12.7 mmol) of ethyl 3-(1-hydroxyprop-2-ylamino)acrylate (III: R=methyl, $R_1$=ethyl) and 1.03 ml (15.2 mmol) of imidazole were added in 30 ml of benzene and stirred. To this, 2.11 g (14 mmol) of t-butyldimethylsilylchloride (IV: $R_2$, $R_3$=methyl, $R_4$=t-butyl) was slowly added dropwise and stirred at room temperature for 8 hours. The solvent was removed under reduced pressure (25° C./10 mmHg), and 80 ml of ethylacetate was added to the residue. Thereafter, the resulting reaction system was washed with 10 ml of 0.1N aqueous hydrochloric acid solution, 10 ml of saturated aqueous sodium bicarbonate solution, 10 ml of water and 5 ml of saturated saline water, in due order and then, dried over magnesium sulfate.

After completion of the reaction, the solvent was removed under reduced pressure (25° C./20 mm Hg), to give 3.47 g of oily object product (yield 95%).

Example 3

Ethyl 3-(1-t-butyldimethylsilyloxyprop-2-ylamino)acrylate (V: R=methyl, $R_1$=ethyl, $R_2$, $R_3$=methyl, $R_4$=t-butyl)

2.72 g (15.7 mmol) of ethyl 3-(1-hydroxyprop-2-ylamino)acrylate (III: R=methyl, $R_1$=ethyl), 2.60 g (17.3 mmol) of t-butyldimethylsilylchloride (IV: $R_2$, $R_3$=methyl, $R_4$=t-butyl) were added in 50 ml of tetrahydrofuran and cooled to 0° C. To this, 1.91 g (18.9 mmol) of triethylamine was slowly added dropwise and stired at room temperature for 7 hours. The solvent was removed under reduced pressure (25° C./20 mm Hg). Filtration was carried out in the same manner as that of Example 2, to give 4.24 g of oily object product (yield 94%).

B. Preparation of the Product

Example 4

Ethyl 2-(2-nitro-3,4,5-trifluoro)benzoyl-3-[(1-t-butyldimethylsilyloxyprop-2-yl)amino]acrylate (I: X, $X_1$=fluoro, R=methyl, $R_1$=ethyl, $R_2$, $R_3$=methyl, $R_4$=t-butyl)

1.65 g (5.74 mmol) of ethyl 3-(1-t-butyldimethylsilyloxyprop-2-ylamino)acrylate (V: R=methyl, $R_1$=ethyl, $R_2$, $R_3$=methyl, $R_4$=t-butyl) and 0.88 ml (6.31 mmol) of triethylamine were added in 100 ml of acetonitrile and cooled to 0° C. To this solution, 1.44 g (6.03 mmol) of 2-nitro-3,4,5-trifluorobenzoyl chloride (IV: X, $X_1$=fluoro) was slowly added dropwise and then stirred for 90 minutes. Precipitate was filtered off.

Thereafter, the remaining filtered solution was dried under reduced pressure (25° C./10 mmHg), to leave residue, to which 50 ml of methylenechloride was subsequently poured. This resulting mixture was washed with 10 ml of saturated aqueous ammonium chloride solution, 10 ml of saturated aqueous sodium bicarbonate solution, 10 ml of water and 5 ml of saturated saline water, in due order and then was dried over magnesium sulfate. Thereafter, the organic solvent was completely removed under reduced pressure (25° C./20 mmHg), to give 2.87 g of oily object product (yield 98%).

Analysis of the product revealed that two isomers were present in a ratio of 4:1 therein.

IR (NaCl) cm$^{-1}$: 1695, 1630, 1550

NMR(CDCl$_3$) ppm: 9.60–10.87(1H, brs), 8.30(1H×1/5, d, J=14.8H), 8.20(1H×4/5, d, J=14.2H), 6.86–6.97(1H, m), 4.02(2H×1/5, q, J=7H), 3.95(2H×4/5, q, J=7H), 3.49–3.77(3H, m), 1.34(3H, d, J=6.5H), 1.13(3H, t, J=7H), 0.89(9H, s), 0.07(6H, s)

Example 5

Ethyl 2-(2-nitro-3,4,5-trifluoro)benzoyl-3-[(1-t-butyldimethylsilyloxyprop-2-yl)amino]acrylate (I: X, $X_1$=fluoro, R=methyl, $R_1$=ethyl, $R_2$, $R_3$=methyl, $R_4$=t-butyl)

2.92 g (10.2 mmol) of ethyl 3-(1-t-butyldimethylsilyloxyprop-2-ylamino)acrylate (V: R=methyl, $R_1$=ethyl, $R_2$, $R_3$=methyl, $R_4$=t-butyl) and 1.13 g (14.2 mmol) of pyridine were added in 50 ml of tetrahydrofuran and cooled to 0° C. To this solution, 2.68 g (11.2 mmol) of 2-nitro-3,4,5-trifluorobenzoyl chloride (IV: X, $X_1$=fluoro) was slowly added dropwise and then stirred for 2 hours. Precipitate was filtered off.

Thereafter, filtration was carried out in the same manner as that of Example 4, so as to give 4.84 g of oily object product (yield 97%).

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. A 2-benzoyl-3-silyloxyaminoacrylate derivative having the formula I or a stereoisomeric form thereof, or a salt thereof:

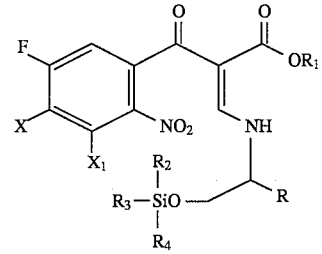

wherein
X is a halogen atom;
$X_1$ is a hologen atom or a nitro group;
R is an alkyl group containing 1 to 4 carbon atoms; and,
$R_1$, $R_2$, $R_3$ and $R_4$ each is independently an alkyl or allyl group containing 1 to 8 carbon atoms.

2. A silylacrylate derivative having the formula V:

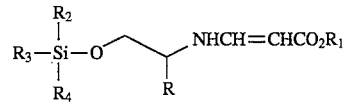

wherein R is an alkyl group containing 1 to 4 carbon atoms; and, $R_1$, $R_2$, $R_3$ and $R_4$ each is independently an alkyl or allyl group containing 1 to 8 carbon atoms.

3. A method for preparing a silylacrylderivative having the following formula V:

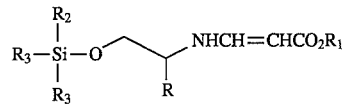

wherein R is an alkyl group containing 1 to 4 carbon atoms; and, $R_1$, $R_2$, $R_3$ and $R_4$ each is independently an alkyl or allyl group containing 1 to 8 carbon atoms, comprising the reaction of an acrylate derivative having the following formula III:

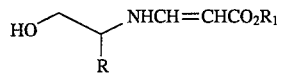

wherein R and $R_1$ each is as defined above, with a trialkylsilyl chloride having the following formula IV:

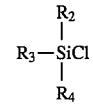

wherein $R_1$, $R_2$, $R_3$ and $R_4$ each is as defined above, at a temperature of 0° to 30° C. for 1 to 24 hours in an organic solvent in the presence of base with stirring.

4. A method set forth as in claim 3, wherein said organic solvent is selected from a group consisting of dimethylformamide, tetrahydrofuran, methylene chloride, acetonitrile, benzene and toluene.

5. A method set forth as in claim 3, wherein said base is selected from a group consisting of pyridine, triethylamine, 2,6-lutidine, 4-dimethylaminopyridine, imidazole, 1,8-diazabicyclo[5.4.0]undec-7-ene and 1,5-diazabicyclo[4.3.0]non-5-ene.

6. A method for preparing a 2-nitrobenzoyl-3-silyloxyaminoacrylate derivative having the following formula I:

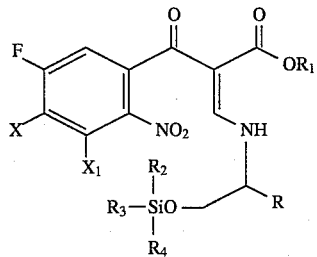

wherein
X is a halogen atom;
$X_1$ is an alkyl group containing 1 to 4 carbon atoms; and,
$R_1$, $R_2$, $R_3$ and $R_4$ each is independently an alkyl or allyl group containing 1 to 8 carbon atoms,
comprising the reaction of a silylacrylate derivative having the following formula V:

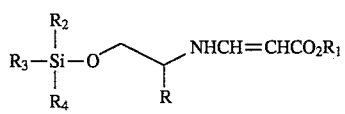

wherein R, $R_1$, $R_2$, $R_3$ and $R_4$ each is as defined above, with a 2-nitrobenzoyl chloride derivative having the following formula VI:

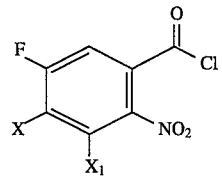

wherein X and $X_1$ each is as defined above, at a temperature of 0° to 100° C. for 0.5 to 3 hours in the presence of base with heating.

7. A method set forth as in claim 6, wherein said organic solvent is selected from a group consisting of methylene chloride, acetonitrile, diethylether, ethylene chloride, dimethylformamide, tetrahydrofuran and chloroform.

8. A method set forth as in claim 6, wherein said base is selected from a group consisting of triethylamine, pyridine, 4-dimethylpyridine, imidazole, 2,6-lutidine, 1,8-diazabicyclo[5.4.0]undec-7-en and 1,5-diazabicyclo[4.3.0]non-5-en.

* * * * *

UNITED STATES PATENT AND TRADEMARK OFFICE
CERTIFICATE OF CORRECTION

PATENT NO. : 5,516,927

DATED : May 14, 1996

INVENTOR(S) : Youseung Kim, Soon Bang Kang and Seonhee Park

It is certified that error appears in the above-indentified patent and that said Letters Patent is hereby corrected as shown below:

On the title page, under [75] Inventors:, change "Yousoung" to --Youseung--, and change "Seonhec" to --Seonhee--.

Signed and Sealed this

Twenty-second Day of October, 1996

Attest:

BRUCE LEHMAN

*Attesting Officer*    *Commissioner of Patents and Trademarks*